(12) United States Patent
Kornbluth et al.

(10) Patent No.: US 11,193,891 B2
(45) Date of Patent: Dec. 7, 2021

(54) RECEPTORS AND SPACERS FOR A FLUORESCENCE-BASED LEAD ION CHEMOSENSOR

(71) Applicant: Robert Bosch GmbH, Stuttgart (DE)

(72) Inventors: Mordechai Kornbluth, Brighton, MA (US); Kaushal Sagar, Seasons Park (SG); Jonathan Mailoa, Cambridge, MA (US); Soo Kim, Cambridge, MA (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 16/722,988

(22) Filed: Dec. 20, 2019

(65) Prior Publication Data
US 2021/0190695 A1    Jun. 24, 2021

(51) Int. Cl.
| G01N 21/77 | (2006.01) |
| G01N 21/64 | (2006.01) |
| C07D 515/14 | (2006.01) |
| C07D 277/22 | (2006.01) |
| G01N 33/52 | (2006.01) |
| G01N 31/22 | (2006.01) |

(52) U.S. Cl.
CPC ........... *G01N 21/77* (2013.01); *C07D 277/22* (2013.01); *C07D 515/14* (2013.01); *G01N 21/6428* (2013.01); *G01N 31/22* (2013.01); *G01N 33/52* (2013.01); *G01N 2021/7786* (2013.01)

(58) Field of Classification Search
CPC .... G01N 21/77; G01N 33/52; G01N 21/6428; G01N 2021/7786; C07D 515/14; C07D 277/22
See application file for complete search history.

(56) References Cited

U.S. PATENT DOCUMENTS

| 6,878,552 B1 | 4/2005 | Mathis |
| 7,309,567 B1 | 12/2007 | Mathis |
| 7,429,651 B2 | 9/2008 | Taing |
| 7,635,573 B2 | 12/2009 | Fischer |
| 7,700,375 B2 | 4/2010 | Keillor |
| 7,713,694 B2 | 5/2010 | Mackintosh |
| 8,198,039 B2 | 6/2012 | Shi |
| 8,211,656 B2 | 7/2012 | Hyde |
| 8,574,914 B2 | 11/2013 | Lippard |
| 8,846,676 B2 | 9/2014 | Almario Garcia |

(Continued)

FOREIGN PATENT DOCUMENTS

| CN | 108864046 A | * 11/2018 | |
| WO | WO-2019137927 A1 | * 7/2019 | ................ A61P 9/10 |

OTHER PUBLICATIONS

Liu et al., "A 1,8-naphthalimide-based fluorescent sensor with high selectivity and sensitivity for Hg2+ in aqueous solution and living cells", May 2019, Anal. Methods. 11, 3150 (Year: 2019).*

(Continued)

*Primary Examiner* — Samuel P Siefke
*Assistant Examiner* — Henry H Nguyen
(74) *Attorney, Agent, or Firm* — Michael Best & Friedrich LLP (57) ABSTRACT

Provided are chemosensor compounds of formula (I) useful for detecting an ion, such as $Pb^{2+}$ in an aqueous sample. Also provided are a chemosensor device including such compounds and methods of use thereof.

18 Claims, 3 Drawing Sheets

(56) References Cited

U.S. PATENT DOCUMENTS

| | | | |
|---|---|---|---|
| 9,101,669 B2 | 8/2015 | Hahn | |
| 9,850,239 B2 | 12/2017 | Do | |
| 10,371,710 B2 | 8/2019 | Wasson | |
| 2010/0304357 A1 | 12/2010 | Meyers | |
| 2011/0287473 A1 | 11/2011 | De Barry | |
| 2012/0270262 A1 | 10/2012 | Lippard | |
| 2016/0169850 A1 | 6/2016 | Magri | |
| 2016/0320400 A1 | 11/2016 | Khan | |
| 2018/0036307 A1* | 2/2018 | Mcwherter | A61P 1/04 |
| 2018/0118791 A1 | 5/2018 | Smith | |
| 2018/0356328 A1* | 12/2018 | Kimura | G01N 15/10 |
| 2019/0192697 A1 | 6/2019 | Rowbottom | |

OTHER PUBLICATIONS

Translation of CN108864046A, Dai, Yu, Nov. 23, 2018 (Year: 2018).*

K. P. Carter, A. M. Young, and A. E. Palmer, "Fluorescent sensors for measuring metal ions in living systems," Chem. Rev., vol. 114, No. 8, pp. 4564-4601, 2014.

H. He, M. A. Mortellaro, M. J. P. Leiner, S. T. Young, R. J. Fraatz, and J. K. Tusa, "A fluorescent chemosensor for sodium based on photoinduced electron transfer," Anal. Chem., vol. 75, No. 3, pp. 549-555, 2003.

T. Petrenko and F. Neese, "Analysis and prediction of absorption band shapes, fluorescence band shapes, resonance Raman intensities, and excitation profiles using the time-dependent theory of electronic spectroscopy," J. Chem. Phys., vol. 127, No. 16, 2007.

* cited by examiner

RECEPTORS AND SPACERS FOR A FLUORESCENCE-BASED LEAD ION CHEMOSENSOR

BACKGROUND

Drinking water quality remains a matter of concern in many parts of the word today. This is primarily stemming from very diverse drinking water sources such as boreholes, lakes, rivers rain water etc. Heavy metal pollution in drinking water is one of the most hazardous type of pollutants which can have adverse effect on the health over prolonged exposures. Lead is one of the common pollutants found in the drinking water which needs monitoring. Other toxic heavy-metals include As, Hg, Cr, and Cd. The World Health Organization guideline value for lead (Pb) is 10 micrograms per liter. This level of pollutant, however, is challenging to detect, especially in a cost-effective way. Therefore, there remain a need for chemical sensors with high sensitivity toward water pollutants, which may be produced at reduced cost.

SUMMARY

In one aspect, the present disclosure provides a compound of formula (I), or salts thereof, wherein $R^1$ is a 5- to 12-membered cyclic group having at least one ring atom being N, O, or S and optionally at least one double bond between two adjacent ring atoms, wherein $R^1$ is optionally substituted with 1, 2, 3, or 4 $R^A$, and wherein $R^1$ is optionally substituted with 1 or 2-(X—$R^2$);

X at each occurrence is independently bond, $CH_2$, O, S, NH, or N($CH_3$);

$R^2$ at each occurrence is independently is a 5- to 12-membered cyclic group optionally having at least one double bond between two adjacent ring atoms, wherein $R^2$ optionally has at least one ring atom being N, O, or S, and wherein $R^2$ is optionally substituted with 1, 2, 3, or 4 $R^B$;

$R^A$ and $R^B$ at each occurrence is independently selected from the group consisting of —$CH_3$, —$CH_2CH_3$, —$CH_2OH$, —$CH_2NH_2$, —$COCH_3$, —COOH, —$CONH_2$, —CN, —OH, —$OCH_3$, —$NH_2$, —$NHCH_3$, —N($CH_3)_2$, —SH, —$SCH_3$, halogen, and halomethyl;

G is a cyclic fluorophore, wherein G is attached to the parent molecule moiety through a ring atom, and wherein G is optionally substituted with -L-T;

L is a linker selected from the group consisting of bond, $C_{1-4}$alkylene, $OC_{1-4}$alkylene, $NHC_{1-4}$alkylene, $SO_2C_{1-4}$alkylene, and $C_{1-4}$alkylene$C_6H_4$;

T is selected from the group consisting of a leaving group, —OH, —$NH_2$, —C(O)OH, protected hydroxyl, protected amino, and protected carboxyl.

In another aspect, the present disclosure provides a chemosensor device, comprising:
a compound as described herein, or a salt thereof,
an optical detector,
a light source, and
a receptacle adapted to contact an aqueous sample.

In yet another aspect, the present disclosure provides a method of detecting an ion in an aqueous sample, comprising:
contacting the aqueous sample with a chemosensor device as described herein;

exposing the aqueous sample to light, whereupon the compound of the chemosensor device binds to the ion, thereby causing the compound to produce a fluorescence signal; and
detecting the fluorescence signal.

Other aspects of the application will become apparent by consideration of the detailed description and accompanying drawings.

DETAILED DESCRIPTION

Before any embodiments of the application are explained in detail, it is to be understood that the application is not limited in its application to the details of construction and the arrangement of components set forth in the following description or illustrated in the following drawings. The application is capable of other embodiments and of being practiced or of being carried out in various ways.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an," and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number therebetween with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "alkylene", as used herein, refers to a divalent group derived from a straight or branched chain hydrocarbon of 1 to 10 carbon atoms, for example, of 1 to 4 carbon atoms. Representative examples of alkylene include, but are not limited to, —$CH_2CH_2$—, —$CH_2CH_2CH_2$—, and —$CH_2CH_2CH_2CH_2$—.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings.

The term "cycloalkyl" as used herein, refers to a carbocyclic ring system containing three to ten carbon atoms and zero heteroatoms, and optionally containing 1 or 2 double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "halogen" or "halo" as used herein, means Cl, Br, I, or F.

The term "halomethyl" as used herein, means a methyl group, in which one, two, or three hydrogen atoms are replaced by halogen. Representative examples of halomethyl include, but are not limited to, chloromethyl, difluoromethyl, and trifluoromethyl.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings.

The term "hydroxyl" as used herein, means an —OH group.

In some instances, the number of carbon atoms in a hydrocarbyl substituent (e.g., alkylene, alkyl, or cycloalkyl) is indicated by the prefix "$C_{x-y}$", wherein x is the minimum and y is the maximum number of carbon atoms in the substituent. Thus, for example, "$C_{1-4}$alkylene" refers to an alkylene containing from 1 to 4 carbon atoms.

One approach for ion sensing is fluorescence-based detection, where the ion attaches to a molecule that causes or quenches a fluorescence. The optical signal (e.g., coupled with electronics such as a photodiode) may be used to measure the ion concentration. A class of sensors based on a fluorophore/spacer/receptor chemistry was used as a sodium sensor. For example, while the fluorophore alone is natively fluorescent upon excitation, no fluorescent is observed in the absence of metal ion binding to the receptor, due to the photoinduced electron transfer (PET) between the receptor and the fluorophore, which competes with fluorescent emission. Upon binding to a metal ion, the receptor energy level is modulated, which quenches the competing PET and "turns on" the fluorescence signal.

The present disclosure relates to fluorescence-based chemical sensors with a short spacer (e.g., methylamine, —CH$_2$NH—) between a rigid ion receptor group and a fluorophore. Remarkably, the sensors as described here may prevent "foldover quenching" encountered in conventional sensors, and may provide improved sensitivity to water pollutants.

In one aspect, the present disclosure provides a compound of formula (I), or salts thereof, $$R^1—CH_2NH-G \quad\quad (I)$$

wherein

R$^1$ is a 5- to 12-membered cyclic group having at least one ring atom being N, O, or S and optionally at least one double bond between two adjacent ring atoms, wherein R$^1$ is optionally substituted with 1, 2, 3, or 4 R$^A$, and wherein R$^1$ is optionally substituted with 1 or 2—(X—R$^2$);

X at each occurrence is independently bond, CH$_2$, O, S, NH, or N(CH$_3$);

R$^2$ at each occurrence is independently is a 5- to 12-membered cyclic group optionally having at least one double bond between two adjacent ring atoms, wherein R$^2$ optionally has at least one ring atom being N, O, or S, and wherein R$^2$ is optionally substituted with 1, 2, 3, or 4 R$^B$;

R$^A$ and R$^B$ at each occurrence is independently selected from the group consisting of —CH$_3$, —CH$_2$CH$_3$, —CH$_2$OH, —CH$_2$NH$_2$, —COCH$_3$, —COOH, —CONH$_2$, —CN, —OH, —OCH$_3$, —NH$_2$, —NHCH$_3$, —N(CH$_3$)$_2$, —SH, —SCH$_3$, halogen, and halomethyl;

G is a cyclic fluorophore, wherein G is attached to the parent molecule moiety through a ring atom, and wherein G is optionally substituted with -L-T;

L is a linker selected from the group consisting of bond, C$_{1-4}$alkylene, OC$_{1-4}$alkylene, NHC$_{1-4}$alkylene, SO$_2$C$_{1-4}$alkylene, and C$_{1-4}$alkyleneC$_6$H$_4$, T is selected from the group consisting of a leaving group, —OH, —NH$_2$, —C(O)OH, protected hydroxyl, protected amino, and protected carboxyl.

R$^1$ may be a rigid cyclic group capable of chelating or complexing with an ion. In some embodiments, R$^1$ includes at least one double bond between two adjacent ring atoms. For example, R$^1$ may contain 1, 2, 3, 4, or 5 double bonds between ring atoms. In some embodiments, R$^1$ is an optionally substituted heteroaryl. For example, R$^1$ may be an optionally substituted thiazole, an optionally substituted diazine (such as 1,2-diazine, 1,3-diazine, or 1,4-diazine), or an optionally substituted pyridine. In some embodiments, R$^1$ is an optionally substituted thiazole.

In some embodiments, R$^A$ is absent. In some embodiments, at least one R$^A$ is present. In some embodiments, R$^1$ is substituted by 1 or 2 R$^A$, each independently selected from —CH$_3$, —CH$_2$CH$_3$, —CH$_2$OH, —CH$_2$NH$_2$, —COCH$_3$, —COOH, —CONH$_2$, —CN, —OH, —OCH$_3$, —NH$_2$, —NHCH$_3$, —N(CH$_3$)$_2$, —SH, —SCH$_3$, halogen, and halomethyl. In some embodiments, R$^1$ is substituted by 1 or 2 R$^A$, each independently selected from —N(CH$_3$)$_2$, —SCH$_3$, and —CF$_3$.

R$^2$ may be a rigid cyclic group optionally having 1, 2, or 3 heteroatoms selected from N, O, and S. In some embodiments, R2 has at least one double bond between two adjacent ring atoms. In some embodiments, R2 is an optionally substituted aryl, an optionally substituted heteroaryl, or an optionally substituted heterocycle having at least one double bond between two adjacent ring atoms. For example, R2 may be an optionally substituted phenyl, an optionally substituted pyrrolidine, or an optionally substituted pyrimidine.

In some embodiments, R$^B$ is absent. In some embodiments, at least one R$^B$ is present. In some embodiments, R$^2$ is substituted by 1 or 2 R$^B$, each independently selected from —CH$_3$, —CH$_2$CH$_3$, —CH$_2$OH, —CH$_2$NH$_2$, —COCH$_3$, —COOH, —CONH$_2$, —CN, —OH, —OCH$_3$, —NH$_2$, —NHCH$_3$, —N(CH$_3$)$_2$, —SH, —SCH$_3$, halogen, and halomethyl. In some embodiments, R$^2$ is substituted by 1 or 2 R$^B$, each independently selected from —N(CH$_3$)$_2$, —SCH$_3$, and —CF$_3$.

In some embodiments, X is bond. In some embodiments, X is O, S, or NH.

In some embodiments, the compounds of formula (I), or salts thereof, have a structure of formula (I-a)

(I-a)

wherein X, R$^2$, and G are as defined in formula (I).

In some embodiments, the compounds have a structure of formula (I-a), in which X is a bond. In some embodiments, the compounds have a structure of formula (I-a), in which R$^2$ is In some embodiments, the compounds of formula (I), or a salt thereof, have a structure of formula (I-b)

(I-b)

wherein R$^A$ and G are as defined in formula (I).

In some embodiments, the compounds have a structure of formula (I-b), in which R$^A$ is —N(CH$_3$)$_2$.

G may be any suitable fluorophore, such that the compound produces a significantly increased fluorescence signal upon the binding of an ion to the compound, as compared to the signal produced by the compound in the absence of the ion binding. For example, the compounds may produce only negligible or even non-detectable fluorescence in the absence of ion binding. Upon binding to an ion, the compounds may produce a stable, readily measurable fluorescence signal.

Suitable fluorophores include, but are not limited to, xanthene derivatives (e.g., fluorescein, rhodamine), benzene, anthracene, naphthalene and derivatives (e.g., dansyl, prodan), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), 1,2-bis(2-aminophenoxy)ethane-N,N,N',N'-tetraacetic acid (BAPTA), 2-(2'-morpholino-2'-oxoethoxy)-N,N-bis(hydroxycarbonylmethyl) aniline (MOBHA), carbazole, diphenylfurane, and 1,8-naphthalimide.

In some embodiments, the compounds have a structure of formula (I), (I-a), or (I-b), in which G is anthracene, benzene, carbazole, diphenylfurane, naphthalene, 1,8-naphthalimide, porphyrin, pyrene, or derivatives thereof. In some embodiments, G is unsubstituted. In some embodiments, G is substitute with a -L-T group as described herein. In some embodiments, G is 1,8-naphthalimide, which is optionally substituted with -L-T. In some embodiments, G is which is optionally substituted with -L-T.

The -L-T group may be capable of forming a covalent bond with a support material or a stationary phase, such as a polymer material. For example, the -L-T group may react with a functional group of a polymer coating on a substrate to form a covalent bond, thereby immobilizing the compounds as described herein onto the substrate.

In some embodiments, L is a bond, $SO_2C_{1-4}$alkylene, or $C_{1-4}$alkylene$C_6H_4$. In some embodiments, L is $CH_2C_6H_4$, such as In some embodiments, L is $SO_2C_2H_4$.

In some embodiments, T is a leaving group, such as chloride, bromide, iodide, tosylate, mesylate, or triflate. In some embodiments, T is —OH, —$NH_2$, or —C(O)OH.

In some embodiments, T is a hydroxyl, an amino, or a carboxyl group protected by a protecting group. The protected groups may be de-protected to provide a —OH, —$NH_2$, or —C(O)OH group, respectively. The term "protecting group" refers to a moiety that prevents chemical reactions from occurring on a heteroatom (such as, N, O, or S) to which that protecting group is attached. Various protecting groups are well known in the art and include those described in detail in Greene's Protective Groups in Organic Synthesis, T. W. Greene and P. G. M. Wuts, $5^{th}$ edition, John Wiley & Sons, 2014, the entirety of which is incorporated herein by reference. For example, suitable amino protecting groups include, but are not limited to, carbobenzyloxy (—NHCO—$OCH_2C_6H_5$ or —NH-Cbz); t-butyloxycarbonyl (—NHCO—$OC(CH_3)_3$ or —NH-Boc); 9-fluorenylmethyloxycarbonyl (—NH-Fmoc), 2,2,2-trichloroethyloxycarbonyl (—NH-Troc), and allyloxycarbonyl (—NH-Alloc). In each of the foregoing, the —NH— represents the nitrogen from the amino group that is being protected. Suitable hydroxyl protecting groups include, but are not limited to, methoxymethyl ether (MOM), tetrahydropyranyl ether (THP), t-butyl ether, allyl ether, benzyl ether, trimethylsilyl (TMS), t-butyldimethylsilyl (TBDMS), acetyl, benzoyl, and pivalic acid ester. Suitable carboxyl protecting groups include, but are not limited to, methyl ester, t-butyl ester, and benzyl ester.

In some embodiments, -L-T is

In some embodiments, G is

In some embodiments, the compounds as described herein is selected from or salt thereof.

In another aspect, the present disclosure provides a chemosensor device, comprising:
a compound as described herein, or a salt thereof,
an optical detector,
a light source, and
a receptacle adapted to contact an aqueous sample.

The compounds as described herein may be used as fluorescence-based chemical sensors (chemosensor compounds). Remarkably, these compounds may prevent "foldover quenching" of the fluorescence signal and may provide improved sensitivity for detecting ions in an aqueous sample.

Figure 1:
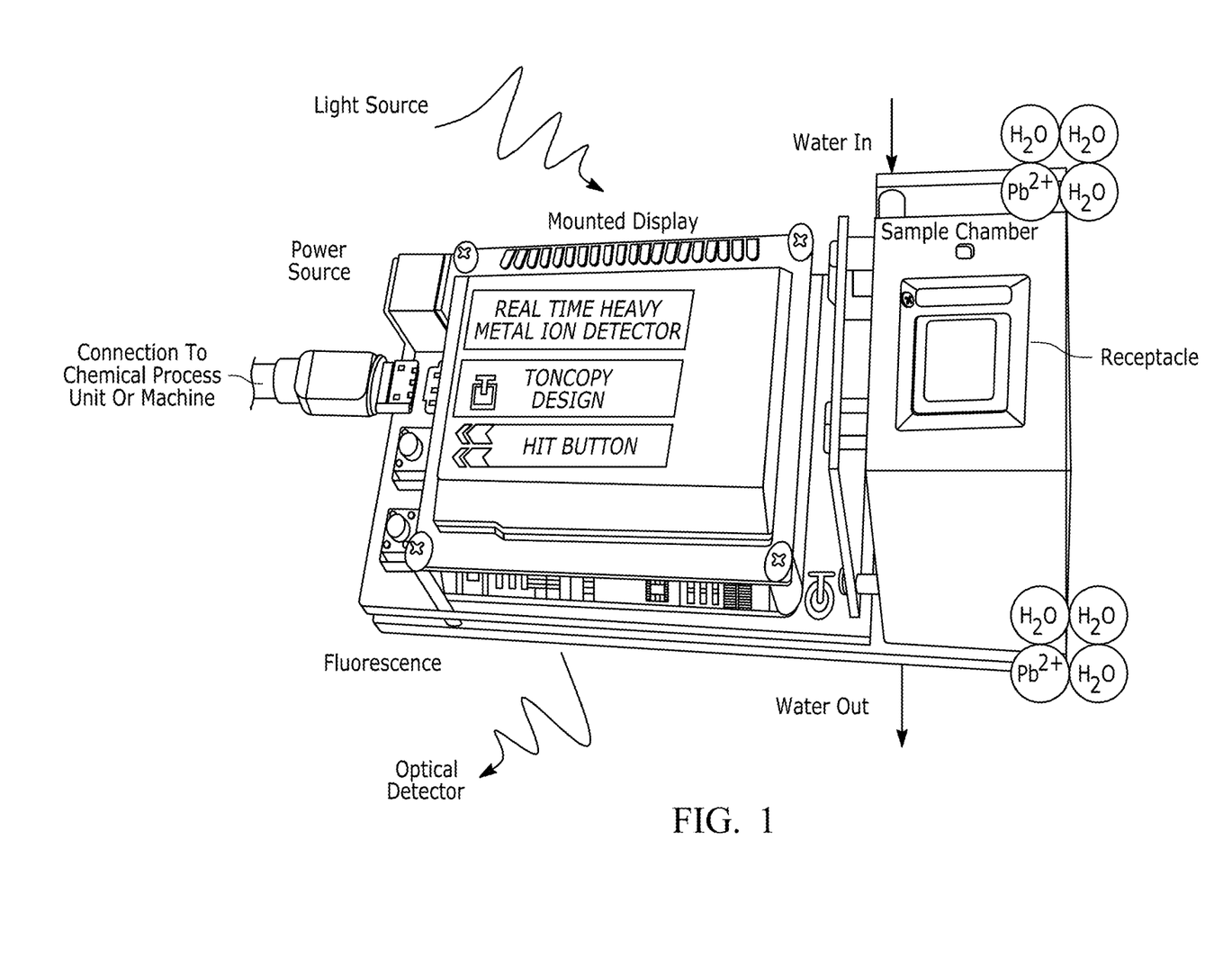
FIG. 1 shows a representative real-time heavy metal ion sensor for water purifiers.

The chemosensor device may include any optical detector capable of detecting and/or measuring fluorescence signal. In some embodiments, the optical detector includes a photodiode. The light source may include any source of visible light. In some embodiments, the light source includes a light-emitting diode (LED). The receptacle may be a pipe, a channel, or a surface that is adapted to contact the aqueous sample. Selections of optical detectors, light sources, and receptacles are within the knowledge of the art. For example, the chemosensor device may include an photodiode as an optical detector, an LED as a light source, and an intake pipe as a receptacle for the sample to be sensed (as shown in FIG. 1).

The chemosensor device may include a surface onto which the chemosensor compounds are immobilized. In some embodiments, the surface comprises a polymer coating or polymer layer. For example, the polymer may be coated onto a solid substrate. Suitable polymers include those having a functional group (such as hydroxyl, amino, or leaving group) capable of reacting with the T group of a compound as described herein to form a covalent bond, thereby causing the compound to be immobilized to the polymer surface or polymer layer. Non-limiting examples of polymers include, for example, aminocellulose.

The chemosensor device may additionally include one or more functional units for the operation of the device, such as a power source, a control panel, a digital processor, a recorder, a data storage unit, and a printer.

In some embodiments, the chemosensor device is connected to a single or multiple chemical process units. For example, real-time analyses of aqueous samples obtained from the chemical process units may be conducted and the results recorded.

In another aspect, the present disclosure provides a machine which includes a chemosensor device as described herein. The machine may be used in an application in which a volume of water is involved and the quality of the water is monitored. For example, the machine may be a water desalinator, a water softener, a water purifier, a water tester, a fuel tester, a coffee maker, a washing machine, an ice maker, a boiler, or a blood tester. In some embodiments, an aqueous sample is obtained from the operation of the machine and fed to the chemosensor to detect ions in the sample.

In yet another aspect, the present disclosure provides a method of detecting an ion in an aqueous sample, comprising:
contacting the aqueous sample with a chemosensor device as described herein;
exposing the aqueous sample to light, whereupon the compound of the chemosensor device binds to the ion, thereby causing the compound to produce a fluorescence signal; and
detecting the fluorescence signal.

The aqueous sample may be obtained from any natural or industrial water sources, or any industrial, medical, or household apparatus that uses, treats, or transports water. In some embodiments, the aqueous sample is obtained from a water desalinator, a water softener, a water purifier, a water tester, a fuel tester, a coffee maker, a washing machine, an ice maker, a boiler, or a blood tester.

In some embodiments, a chemosensor device as described herein, or a machine including such device, is connected to a single or multiple chemical process units, and the method of detecting an ion is conducted in a continuous manner. For example, the aqueous sample may be continuously fed into the device or machine, and the detection method may be conducted continuously to record and/or monitor the quality of water in the sample. The continuous feeding, detecting, recording, and/or monitoring process may be automated and carried out according to a programmable schedule.

In some embodiments, the chemosensor device is adapted for detecting an ion selected from $Pb^{2+}$, $Ca^{2+}$, $K^+$, $Na^+$, $Cr^{3+}$, $Hg^{2+}$, $Cd^{2+}$, $Mg^{2+}$, $As^{3+}$, $As^{5+}$, and a combination thereof. In some embodiments, the ion is $Pb^{2+}$, $Ca^{2+}$, $Hg^{2+}$, $Cd^{2+}$, $Mg^{2+}$, or a combination thereof. In particular embodiments, the ion is $Pb^{2+}$, such as the $Pb^{2+}$ in a natural water source, or the $Pb^{2+}$ in a sample obtained from a water desalinator, a water softener, a water purifier, a water tester, a fuel tester, a coffee maker, a washing machine, an ice maker, a boiler, or a blood tester.

Example

Figure 2:
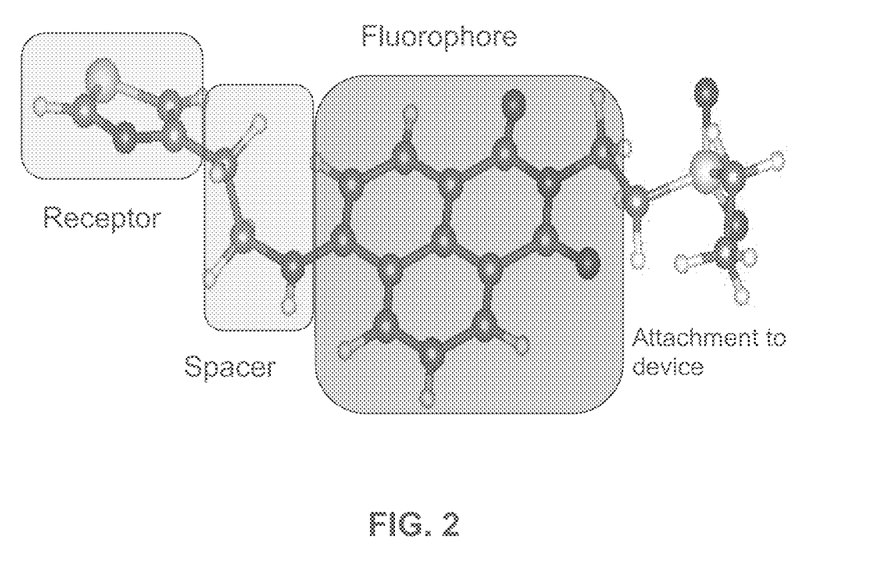
FIG. 2 shows a representative receptor-spacer-fluorophore sensor described herein.

Binding energies and fluorescence spectra of a variety of spacers and receptors for a lead ion ($Pb^{2+}$) binding are simulated by computer modeling. As an examples, the studied molecules have a 1,8-naphthalimide fluorophore, a methylamine or ethylamine spacer, and an optionally substituted thiazol group as a receptor for $Pb^{2+}$ binding (FIG. 2). The molecules described herein may be synthesized using standard precursors (including those commercially available) using standard organic synthesis techniques known in art.

The binding strength is related to the dissociation constant (and hence the titration curve) based on the known equation $K_d = c^\circ e^{\Delta G/k_B T}$, where $K_d$ is the dissociation constant, $c^\circ$ the standard reference concentration (1 mol), $\Delta G$ the free energy of binding (usually on the order of −50 to −1,000 meV), and $k_B T$ the Boltzmann constant times the absolute temperature. Other corrections may be added for correlated effects (the Hill coefficient). The binding energy is computed as the total energy of the molecule with the ion, minus the total energy of the molecule and ion separately (i.e., $\Delta E_{binding} = E_{0,total} - $ ($E_{0,molecule}+E_{0,ion}$), where $E_0$ is the calculated internal energy that can be obtained from simulation).

ORCA quantum-chemistry code are used for these calculations. The procedures for the calculations use multiple basis sets. The geometry is optimized using a local-density approximation (LDA) with the implicit solvation model CPCM (water), and a basis set def2-svp (Karlsruhe valence double-zeta with polarization). The total energy is computed using RI-MP2, again with CPCM/def2-svp. A basis set correction is added under LDA (no solvation) up to def2-qzvpp (quadruple-zeta basis set), and an independent correlation correction is added under def2-svp (no solvation) from DLPNO-CCSD(T). These are the binding energies shown in Table 1. The fluorescence is computed without solvation, using geometry of BLYP/def2-svp, a Hessian from the ground state using BLYP/def2-svp, and a spectrum using TD-DFT BLYP/def2-svp. The fluorescence is computed using the ORCA ASA module.

The simulation methods are validated as follows. The binding energies are benchmarked against the literature for known receptor/ion pairs. These are often 10-30× larger than expected, because the formation energies are computed using implicit solvation rather than explicit solvation. Nonetheless, the results give qualitative ordering of binding strengths accurately. The optical spectra are benchmarked against a naphthalimide-methylamine-thiazol molecule. BLYP/def2-svp successfully predicts fluorescence if and only if the Pb ion is bound, in agreement with experimental measurements.

It is not obvious from the receptor-spacer chemistry which would be useful and which would not. Remarkably, by performing the screening, some important features for an effective fluorophore may be identified. All the studied molecules show a calculated fluorescence when the Pb ion is bound in the minimum-energy site, and no fluorescence when the Pb is not bound (with a partial exception of pyrimidinyl-ethanolamine as receptor-spacer). All receptor-spacer chemistries indicate an optimal binding site of the spacer's nitrogen and one or more of the nitrogen and sulfur atoms of the receptor.

Figure 3:
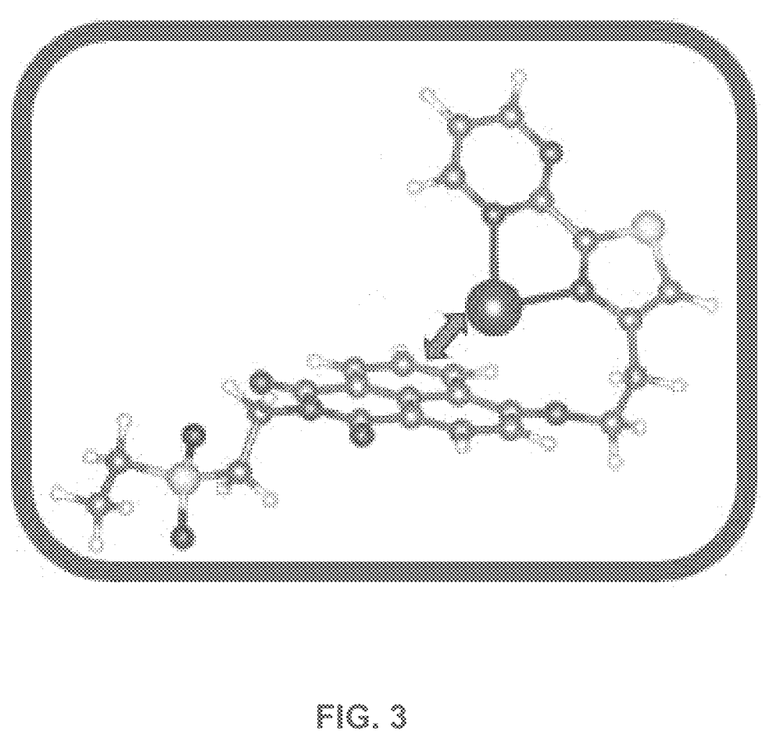
FIG. 3 shows a simulated binding configuration of a chemosensor having pyrimidinyl-ethanolamine as receptor-spacer groups. The simulation shows that the molecule would not fluoresce despite Pb binding, due to proximity between the ion and the fluorophore.

The geometry optimizations indicate that all chemistries with the ethylamine spacer created a folded configuration, where the receptor folds over to be closer to the fluorophore. The energy gain of this folding is approximately 100 meV per molecule (LSD CPCM/def2-svp), indicating that it is a stable ground state. In at least one receptor (pyrimidinyl-ethanolamine), the subsequent Pb binding and fluorescence calculation indicate a stable binding site that is close to the fluorophore (FIG. 3), which causes PET and quenches fluorescence. In general, therefore, receptor/spacer pairs that allow proximity between an ion binding site and a fluorophore may be avoided. Specifically, the number of bonds that can rotate (i.e. single bonds) may be minimized to prevent this "fold-over quenching". Among the non-foldover structures, a high sensitivity (high binding strength) requires a longer measurement time, so various compounds may be useful depending on the context—a quick measurement with low sensitivity may use the "weak receptor" structures, while a longer measurement with high sensitivity may use the "strong receptor" structures.

The trends of binding energies indicate that the chief descriptor of binding strength is the number of electronegative atoms (e.g., N and S) bound to the ion. The highest sensitivity, therefore, may occur when three atoms are proximate to the binding site, and lower sensitivity (and therefore faster measurement time) when only two atoms are proximate to the binding site. The electronegative atoms may be on the same side of the molecule (in some conformer) in order to bind to the cation. Depending on the size, sensitivity, and lifetime, the sensor device may be adjusted for use with different types of chemosensor molecules as indicated in Table 1.

TABLE 1

| receptor-spacer moiety | Structure | Pb binding energy (eV) | Effect |
|---|---|---|---|
| (Thiazol-4-yl)methanamino | | −1.681 | Weak-Moderate receptor |
| ({2-[(Methylthio)methyl]-1,3-thiazol-4-yl]methyl)amino | | −2.22 | Strong receptor |
| 1-[2-(2-Pyrimidinyl)-1,3-thiazol-4-yl]methanamino | | −2.102 | Strong receptor |
| 1-(2-Pyrrolidin-1-yl-1,3-thiazol-4-yl)methanamino | | −1.907 | Moderate receptor |

TABLE 1-continued

| receptor-spacer moiety | Structure | Pb binding energy (eV) | Effect |
|---|---|---|---|
| (2-(N,N-dimethylamino)thiazol-4-yl)methanamino | | −1.837 | Moderate receptor |
| (2-Methylthiazol-4-yl)methanamino | | −1.609 | Weak receptor |
| {2-[4-(Trifluoromethyl)phenyl]-1,3-thiazol-4-yl]methylamino | | −1.524 | Weak receptor |
| 2-[2-(2-Pyrimidinyl)-1,3-thiazol-4-yl]ethanamino | | −2.427 | Fold-over |
| 2-(2-Isopropyl-1,3-thiazol-4-yl)ethanamino | | −1.769 | Fold-over |
| 2-(2-Methyl-1,3-thiazol-4-yl)ethylamino | | −1.668 | Fold-over |
| (2-{2-(Methylthio)methyl]-1,3-thiazol-4-yl}ethyl)amino | | −2.145 | Fold-over |
| 2-(1,3-Thiazol-4-yl)ethanamino | | −1.599 | Fold-over |
| 2-(2-Amino-(1,3-thiazol-4-yl))ethanamino | | −1.747 | Fold-over |

Example embodiments include the following:

Example 1. A compound of formula (I), or salts thereof, $$R^1-CH_2NH-G \quad (I)$$

wherein

R1 is a 5- to 12-membered cyclic group having at least one ring atom being N, O, or S and optionally at least one double bond between two adjacent ring atoms, wherein R1 is optionally substituted with 1, 2, 3, or 4 RA, and wherein R1 is optionally substituted with 1 or 2 —(X—R2);

X at each occurrence is independently bond, CH2, O, S, NH, or N(CH3);

R2 at each occurrence is independently is a 5- to 12-membered cyclic group optionally having at least one double bond between two adjacent ring atoms, wherein R2 optionally has at least one ring atom being N, O, or S, and wherein R2 is optionally substituted with 1, 2, 3, or 4 RB;

RA and RB at each occurrence is independently selected from the group consisting of —CH3, —CH2CH3, —CH2OH, —CH2NH2, —COCH3, —COOH, —CONH2, —CN, —OH, —OCH3, —NH2, —NHCH3, —N(CH3)2, —SH, —SCH3, halogen, and halomethyl;

G is a cyclic fluorophore, wherein G is attached to the parent molecule moiety through a ring atom, and wherein G is optionally substituted with -L-T;

L is a linker selected from the group consisting of bond, C1-4alkylene, OC1-4alkylene, NHC1-4alkylene, SO2C1-4alkylene, and C1-4alkyleneC6H4, T is selected from the group consisting of a leaving group, —OH, —NH2, —C(O)OH, protected hydroxyl, protected amino, and protected carboxyl.

Example 2. The compound of claim Example 1, or a salt thereof, wherein R1 is an optionally substituted heteroaryl.

Example 3. The compound of any one of Examples 1-2, wherein R1 is an optionally substituted thiazole.

Example 4. The compound of any one of Examples 1-3, or a salt thereof, wherein R2 is an optionally substituted aryl, an optionally substituted heteroaryl, or an optionally substituted heterocycle having at least one double bond between two adjacent ring atoms.

Example 5. The compound of Example 1, or a salt thereof, having a structure of formula (I-a)

(I-a)

Example 6. The compound of Example 5, or a salt thereof, wherein X is bond.

Example 7. The compound of any one of Examples 5-6, or a salt thereof, wherein R2 is Example 8. The compound of Example 1, of a salt thereof, having a structure formula (I-b)

(I-b)

Example 9. The compound of Example 8, or a salt thereof, wherein RA is —N(CH3)2.

Example 10. The compound of any one of Examples 1-9, or a salt thereof, wherein G is anthracene, benzene, carbazole, diphenylfurane, naphthalene, 1,8-naphthalimide, porphyrin, or pyrene; and wherein G is optionally substituted with -L-T.

Example 11. The compound of any one of Examples 1-10, or a salt thereof, wherein G is 1,8-naphthalimide optionally substituted with -L-T.

Example 12. The compound of any one of Examples 1-11, or a salt thereof, wherein G is which is optionally substituted with one or more -L-T.

Example 13. The compound of any one of Examples 1-12, or a salt thereof, wherein -L-T is Example 14. The compound of Example 1, selected from the group consisting of:

or salt thereof.

Example 15. A chemosensor device, comprising: a compound of Example 1, or a salt thereof, an optical detector, a light source, and a receptacle adapted to contact an aqueous sample.

Example 16. The chemosensor device of Example 15, wherein the device is connected to a single or multiple chemical process units.

Example 17. A machine comprising a chemosensor device of Example 15, wherein the machine is a water desalinator, a water softener, a water purifier, a water tester, a fuel tester, a coffee maker, a washing machine, an ice maker, a boiler, or a blood tester.

Example 18. A method of detecting an ion in an aqueous sample, comprising: contacting the aqueous sample with a chemosensor device of Example 15; exposing the aqueous sample to light, whereupon the compound of the chemosensor device binds to the ion, thereby causing the compound to produce a fluorescence signal; and detecting the fluorescence signal.

Example 19. The method of Example 18, wherein the aqueous sample is obtained from a water desalinator, a water softener, a water purifier, a water tester, a fuel tester, a coffee maker, a washing machine, an ice maker, a boiler, or a blood tester.

Example 20. The method of Example 18, wherein the chemosensor device is connected to a single or multiple chemical process units, and wherein the method is conducted in a continuous manner.

Example 21. The method of Example 14, wherein the ion is Pb2+, Ca2+, K+, Na+, Cr3+, Hg2+, Cd2+, Mg2+, As3+, As5+, or a combination thereof.

Various features and advantages of the application are set forth in the following claims.

What is claimed is:

1. A chemosensor device, comprising:
   a compound of formula (I), or a salt thereof,

R$^1$—CH$_2$NH-G      (I)

wherein
   R$^1$ is thiazole optionally substituted with R$^A$ or —(X—R$^2$);
   X at each occurrence is independently a single bond, CH$_2$, O, S, NH, or N(CH$_3$);
   R$^2$ at each occurrence is independently a 5- to 12-membered cyclic group optionally having at least one double bond between two adjacent ring atoms, wherein R$^2$ optionally has at least one ring atom being N, O, or S, and wherein R$^2$ is optionally substituted with 1, 2, 3, or 4 R$^B$;
   R$^A$ and R$^B$ at each occurrence is independently selected from the group consisting of —CH$_3$, —CH$_2$CH$_3$, —CH$_2$OH, —CH$_2$NH$_2$, —COCH$_3$, —COOH, —CONH$_2$, —CN, —OH, —OCH$_3$, —NH$_2$, —NHCH$_3$, —N(CH$_3$)$_2$, —SH, —SCH$_3$, halogen, and halomethyl;
   G is a cyclic fluorophore, wherein G is attached to R$^1$—CH$_2$NH through a ring atom, and wherein G is optionally substituted with -L-T;
   L is a linker selected from the group consisting of a single bond, C$_{1-4}$alkylene, OC$_{1-4}$alkylene, NHC$_{1-4}$alkylene, SO$_2$C$_{1-4}$alkylene, and C$_{1-4}$alkyleneC$_6$H$_4$,
   T is selected from the group consisting of a leaving group, —OH, —NH$_2$, —C(O)OH, protected hydroxyl, protected amino, and protected carboxyl,
   an optical detector,
   a light source, and
   a receptacle adapted to contact an aqueous sample.

2. The chemosensor device of claim 1, wherein the device is connected to a single or multiple chemical process units.

3. A machine comprising a chemosensor device of claim 1, wherein the machine is a water desalinator, a water softener, a water purifier, a water tester, a fuel tester, a coffee maker, a washing machine, an ice maker, a boiler, or a blood tester.

4. The chemosensor device of claim 1, wherein R$^2$ is an optionally substituted aryl, an optionally substituted heteroaryl, or an optionally substituted heterocycle having at least one double bond between two adjacent ring atoms.

5. The chemosensor device of claim 1, wherein the compound has a structure of formula (I-a)

(I-a)

6. The chemosensor device of claim 5, wherein X is a single bond.

7. The chemosensor compound of claim 5, or a salt thereof, wherein R$^2$ is

8. The chemosensor device of claim 1, wherein the compound has a structure formula (I-b)

(I-b)

9. The chemosensor device of claim 8, wherein R$^A$ is —N(CH$_3$)$_2$.

10. The chemosensor device of claim 1, wherein G is anthracene, benzene, carbazole, diphenylfurane, naphthalene, 1,8-naphthalimide, porphyrin, or pyrene; and wherein G is optionally substituted with -L-T.

11. The chemosensor device of claim 1, wherein G is 1,8-naphthalimide optionally substituted with -L-T.

12. The chemosensor device of claim 1, wherein G is which is optionally substituted with one or more -L-T.

13. The chemosensor device of claim 1, wherein -L-T is

14. The chemosensor device of claim 1, wherein the compound is selected from the group consisting of:

or salt thereof.

15. A method of detecting an ion in an aqueous sample, comprising:

contacting the aqueous sample with a chemosensor device of claim 1;

exposing the aqueous sample to light, whereupon the compound of the chemosensor device binds to the ion, thereby causing the compound to produce a fluorescence signal; and detecting the fluorescence signal.

16. The method of claim 15, wherein the aqueous sample is obtained from a water desalinator, a water softener, a water purifier, a water tester, a fuel teste, a coffee maker, a washing machine, an ice maker, a boiler, or a blood tester.

17. The method of claim 15, wherein the chemosensor device is connected to a single or multiple chemical process units, and wherein the method is conducted in a continuous manner.

18. The method of claim 15, wherein the ion is $Pb^{2+}$, $Ca^{2+}$, $K^+$, $Na^+$, $Cr^{3+}$, $Hg^{2+}$, $Cd^{2+}$, $Mg^{2+}$, $As^{3+}$, $As^{5+}$, or a combination thereof.

* * * * *